United States Patent [19]

Helland

[11] Patent Number: 5,385,579
[45] Date of Patent: Jan. 31, 1995

[54] MYOCARDIAL BODY IMPLANTABLE LEAD

[75] Inventor: John R. Helland, Santa Clarita, Calif.

[73] Assignee: Siemens Pacesetter, Inc., Sylmar, Calif.

[21] Appl. No.: 40,070

[22] Filed: Mar. 30, 1993

[51] Int. Cl.⁶ ............................................. A61N 1/05
[52] U.S. Cl. ................................................. 607/130
[58] Field of Search ................. 607/9, 116, 120–121, 607/129, 130, 131, 132

[56] References Cited

U.S. PATENT DOCUMENTS

| | | | |
|---|---|---|---|
| 3,035,583 | 5/1962 | Hirsch et al. | 607/132 |
| 3,244,174 | 4/1966 | Wesby et al. | 607/132 |
| 3,749,101 | 7/1973 | Williamson | 607/121 |
| 3,880,169 | 4/1975 | Starr et al. | 607/129 |
| 4,010,758 | 3/1977 | Rockland et al. | 607/131 |
| 4,136,702 | 1/1979 | Trabucco | 607/130 |
| 4,827,940 | 5/1989 | Mayer et al. | 607/131 |

FOREIGN PATENT DOCUMENTS

| | | | |
|---|---|---|---|
| 0388480 | 9/1990 | European Pat. Off. | 607/120 |
| 3523226 | 1/1987 | Germany | 607/129 |
| 0655394 | 4/1979 | U.S.S.R. | 607/130 |
| 1019533 | 12/1991 | WIPO . | |

OTHER PUBLICATIONS

Williams, W. G. et al., "Permanent Cardiac Pacing in Infants and Children," *PACE*, vol. 1, pp. 439–447 (Oct.–Dec. 1978).

Williams, W. G. et al., "Exit Block in Children with Pacemakers," *Clinical Progress in Electrophysiology and Pacing*, vol. 4, No. 5, pp. 478–488 (1986).

DeLeon, Serafin Y. et al., "Exit Block in Pediatric Cardiac Pacing," *J. Thorac Cardiovasc Surg*, pp. 905–910 (1990).

DeLeon, Serafin Y. et al., "Comparison of the Sutureless and Suture-Type Epicardial Electrodes in Pediatric Cardiac Pacing," *The Society of Thoracic Surgeons*, pp. 273–276 (1981).

Michalik, Richard E. et al., "Experience with a New Epimyocardial Pacing Lead in Children," *PACE*, vol. 7, pp. 831–838 (Sep.–Oct. 1984, Part V).

Gillette, Paul C. et al., "Transvenous Pacing in Pediatric Patients," *Progress in Cardiology*, pp. 843–847 (1982).

Serwer, Gerald A. M.D. et al., "Concurrent Failure of Active and Redundant Ventricular Epicardial Electrodes in Children," *Journal of Interventional Cardiology*, vol. 2, No. 1, pp. 43–47 (1989).

Henglein, Dagmar et al., "Long-Term Follow-up of Pulse Width Threshold of Transvenous and Myo-epicardial Leads," *PACE*, vol. 7, pp. 203–214 (Mar.–Apr. 1984).

Ott, David A., "Epicardial Pacemaker Implantation," *Pediatric Arrhythmias: Electrophysiology and Pacing*, pp. 575–579, Chapter 20 (W. B. Saunders 1990).

Korhonen, Ulla et al., "One Turn More: Threshold Superiority of 3-Turn Versus 2-Turn Screw-In Myocardial Electrodes," *PACE*, vol. 7, pp. 678–682 (Jul.–Aug. 1984).

Karpawich, Peter P. et al., "A New Low Threshold Platinized Epicardial Pacing Electrode: Comparative Evaluation in Immature Canines," *PACE*, vol. 11, pp. 1139–1148 (Aug. 1988).

Serwer, G. A. M.D., et al., "Epicardial Ventricular Pacemaker Electrode Longevity in Children," *The American Journal of Cardiology*, vol. 61, pp. 104–106 (Jan. 1, 1988).

Kugler, John et al., "Comparison of Two Myoepicardial Pacemaker Leads: Follow-up in 80 Children, Adolescents, and Young Adults," *PACE*, vol. 11, pp. 2216–2222 (Dec. 1988).

*Primary Examiner*—William E. Kamm
*Attorney, Agent, or Firm*—Malcolm J. Romano; Lisa P. Weinberg

[57] ABSTRACT

A myocardial lead having a tissue stimulating electrode attached via an insulated conductor to an epicardial pad the electrode embedded in the myocardial tissue of either the ventricles or the atria, for use as a pacing and/or sensing electrode. The myocardial electrode is configured to be pulled into position with a suture needle and thread. The myocardial electrode of the lead is designed to be highly reliable, to reduce exit block and fibrotic tissue growth, and to be utilized for extended periods even though designed to be implanted within the relatively thin myocardial muscle of a pediatric patient.

33 Claims, 2 Drawing Sheets

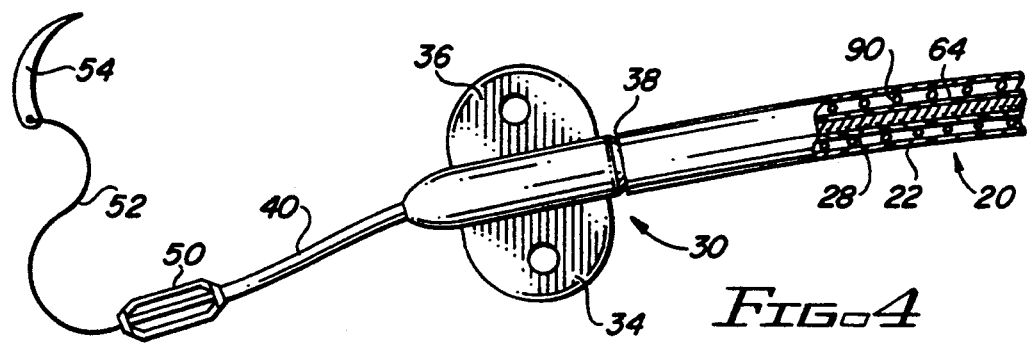
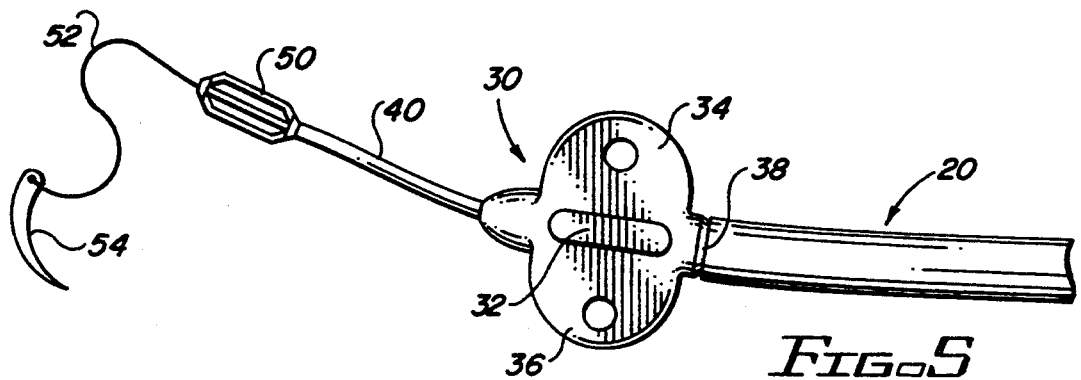
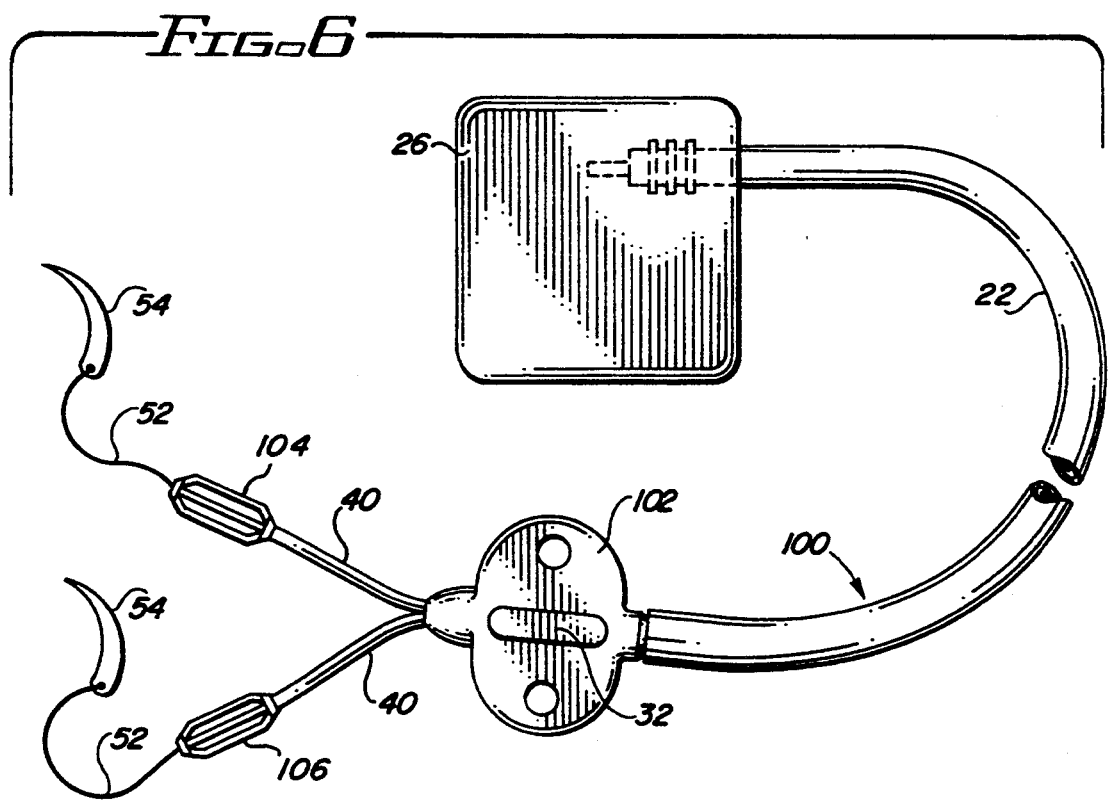

1

MYOCARDIAL BODY IMPLANTABLE LEAD

BACKGROUND OF THE INVENTION

The present invention relates generally to the field of implantable leads and pacing systems for monitoring and controlling the heart. More specifically, the present invention is directed to a myocardial tissue stimulating electrode and lead which interconnects to a pacing system, the myocardial stimulating electrode being particularly adapted for implant and use in infants and small children.

There are two general approaches to implanting a pacing lead in a recipient of a pacing system. The first approach utilizes a pacing lead inserted transvenously, which extends into an abuts an interior endocardial surface of the wall of the heart. Alternatively, pacing systems may include an epicardial lead with an electrode which is affixed in the myocardial tissue of the heart, interconnected via the epicardial lead to the pacemaker. Epicardial pacing is often the required approach for use with pediatric patients because of congenital or surgically induced anatomical considerations and/or due to the size of the pacemaker itself, the size of a transvenous pacing lead as compared to the veins of the pediatric patient, or problems associated with the pacing leads interfering with the tricuspid valve.

However, there are problems associated with epicardial pacing relating to the design of the epicardial lead, including failure of the electrode and resultant pacing threshold "exit block," as well as the limitations on the expected operative life of the epicardial leads and electrodes. It should be noted that there are three basic types of electrode designs for epicardial leads. The first design is referred to as a "sutured lead" and typically includes either a "button," "patch," or "needle-like" electrode which is sutured onto the epicardial surface, or into the myocardium by passing the suture through the base of the electrode and into the adjacent epicardial tissue.

A second type of epicardial lead is a "sutureless" lead, which includes a fish hook or barbed design electrode formed from a metallic element having sufficient structural capability to allow insertion and self-retention in the epicardial tissue. A third type of epicardial lead is also a "sutureless" type electrode and is a screw-in electrode which incorporates an electrode formed into a cork screw configuration adapted to be screwed into the epicardial tissue. These types of screw-in electrode designs may include two or three convolutions, having various sizes and pitch lengths.

For all of the above types of electrodes, there are several different failures which may occur. The first type of failure is associated with an elevated threshold and a high electrode impedance. This type of failure may also be termed as an "exit block" failure. Exit block occurs when a functioning cardiac pacemaker and intact lead system are unable to transmit sufficient energy to the myocardium for consistent cardiac pacing. A second type of failure is associated with electrodes that will not pace at any output of the pacing system. This may occur, for example, because of the failure of the electrode, electrode evulsion, or fracture of the wire interconnecting the pacing generator and the electrode. A third type of failure consists of electrodes having a high threshold but a low electrode impedance. This type of failure may be due to either an insulation fracture or erosion of the stimulating portion of the electrode into the ventricular cavity.

A number of studies have addressed the problems associated with lead failures and pacing systems especially in pediatric patients for various types of epicardial lead electrode configurations. The studies have found that one of the major problems with these types of systems is the high incidence of failure. One study found that lead failures, caused for example by electrode fracture, occurred on an average of twenty eight months after implant. As a result, infants receiving an epicardial electrode pacing system almost always require subsequent surgery within several years and frequently within the first two years. Due to the limitations of the design and failure rate of the epicardial lead, it is extremely unlikely that a pacing system using an epicardial lead of a current design will last until the patient reaches adulthood.

In view of the foregoing limitations of presently available epicardial electrodes and pacing systems, an alternative design for the epicardial electrode lead which provides the capability of enhanced reliability and extended life expectancy is very desirable.

SUMMARY OF THE INVENTION

The present invention is directed to a myocardial lead and a myocardial tissue stimulating electrode which is embedded in the myocardial tissue of either the ventricles or the atria. The myocardial electrode is attached via an insulated conductor to an epicardial pad, and is configured to be pulled into position with a suture needle and thread. As a result, the myocardial electrode is embedded in the myocardial tissue and spaced a short distance from the epicardial pad, which is located on, and attached to, the epicardial tissue. The myocardial electrode can have several different designs intended to provide long term intimate and low fibrotic contact to the myocardial tissue. The myocardial electrode is designed to be highly reliable, to reduce exit block and fibrotic tissue growth, and to be utilized for extended periods even though designed to be implanted within the relatively thin myocardial muscle of a pediatric patient.

BRIEF DESCRIPTION OF THE FIGURES

FIG. 4 depicts a top view of the end of the lead and the myocardial electrode affixed to the thread and suture needle according to the present invention;

FIG. 5 depicts a view of the bottom portion of the end of the lead and myocardial electrode of FIG. 5; and FIG. 6 depicts another alternative embodiment of the epicardial lead including more than one myocardial electrode.

DETAILED DESCRIPTION OF THE PREFERRED EMBODIMENT

Figure 1:
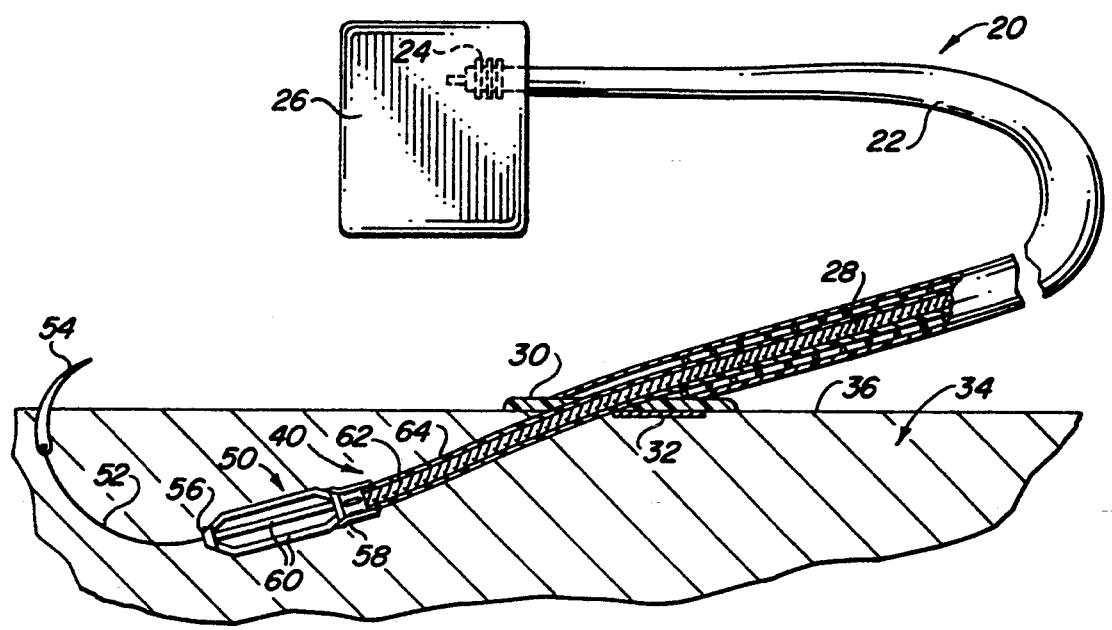
FIG. 1 depicts a pacemaker and an epicardial lead including the implanted myocardial electrode disposed within the myocardium.

FIG. 1 depicts a myocardial lead 20 according to the present invention. The myocardial lead 20 includes a lead body 22 having a connector 24 located at the proximal end of the lead body 22. The connector 24 is inserted and electrically connected to a pulse generating means such as a pacemaker 26. The lead body 22 primarily consists of an insulated conductor 28. At the distal end of the lead body 22 is an epicardial pad 30, which may include an anode electrode 32 on its lower surface in intimate contact with the epicardial tissue 36 of the myocardium 34.

The myocardial lead 20 includes a short, insulated conductor segment 40 extending from the epicardial pad 30. The conductor segment 40 is preferably an insulated helically wound coil which interconnects to, or is a continuation of, the insulated conductor 28, extending through the epicardial pad 30 to a myocardial electrode 50. The myocardial electrode 50 is shown embedded within the myocardium 34. A suture thread 52 is tied to the tip or distal end 56 of the myocardial electrode 50, and connects to a suture needle 54. The suture needle 54 and suture thread 52 are utilized to insert and pull the myocardial electrode 50 into the myocardial tissue. Following insertion of the myocardial electrode 50, the epicardial pad 30 is securely affixed to the epicardial tissue, either utilizing an adhesive or by suture stitching in a known manner.

Figure 2:
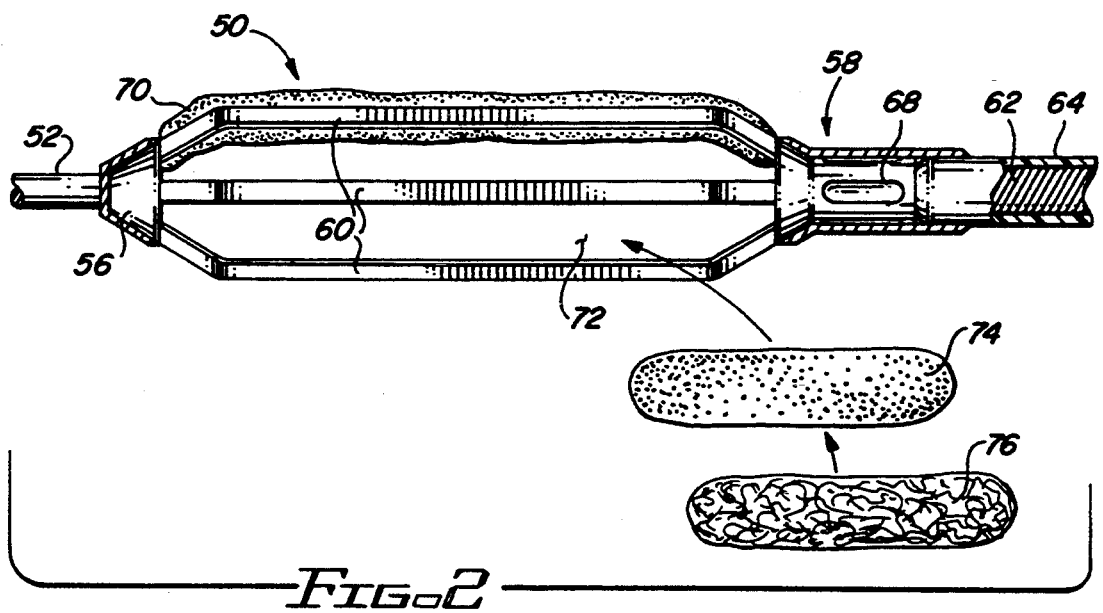
FIG. 2 depicts a detailed enlarged view of the myocardial electrode of FIG. 1.

FIG. 2 depicts an enlarged view of the myocardial electrode 50 of FIG. 1. The detailed design depicted in FIG. 2 includes one or more exposed wires or struts 60. Each of the struts 60 is preferably a single or multiple strand conductive wire formed from a titanium, platinum or platinum-iridium material. The struts 60 may further include a particle coating. Examples of coatings include platinum black, titanium nitride, metal oxides, as well as a metal nitride coating. The coating is intended to enhance electrical efficiency and may help minimize the fibrotic tissue growth response.

The struts 60 are interconnected at their proximal ends 58 via a connector crimp element 68 to a conductor 62 encased within an insulation coating 64, which combine to define the conductor segment 40 of FIG. 1. As previously indicated, the conductor 62 may simply be an extension of the conductor 28 of the lead body 22. The distal or tip ends 56 of the struts 60 may be interconnected, for example by tying with an appropriate biocompatible thread, or by laser welding or by mechanical crimping. The tip ends 56 of the struts 60 are also connected to the suture thread 52 in a manner allowing the suture thread to pull the myocardial electrode 50 through a passageway formed in the myocardial tissue by the suture needle 54.

As shown on the topmost strut 60 in FIG. 2, the myocardial electrode 50 may further include an erodible anti-inflammatory material 70 coated on the struts 60. Alternatively or in addition an anti-inflammatory material may be formed into a semi-gelatinous tablet 74 which is placed between the respective struts 60, such that the tablet 74 is retained by the struts 60 during the insertion of the myocardial electrode 50 into the myocardial tissue.

Furthermore, as also shown in FIG. 2, the myocardial electrode 50 may include a porous tissue ingrowth matrix 76 formed from a material allowing tissue ingrowth and permanent affixation of the myocardial electrode 50 within the tissue of the myocardium. Each of these alternatives could be combined and incorporated into the design of the struts 60. For example, the porous tissue ingrowth matrix may be formed from an electrically conductive mesh and electrically joined to the struts 60, for example by welding, to increase the operative electrical surface area of the myocardial electrode. Further, the matrix 76 may be inserted and electrically connected to the struts 60 and then the entire electrode 50 can be coated with the anti-inflammatory material 70.

The connection of the struts 60 at their distal ends 56 may alternatively be formed by tying the respective ends 56, utilizing a bio-absorbable thread. Upon absorption of the bio-absorbable thread, the distal ends 56 of the struts 60 will essentially be allowed to space themselves from one another, in a manner allowing their mutual separation during the course of normal growth of the heart. When this alternative design is implanted in an infant's myocardium, which may be only 1-5 mm in thickness, the tissue ingrowth between the struts 60 will grow with the heart, allowing the struts 60 to space themselves apart or far out as the myocardial wall thickness increases by 2-3 cm. The most significant advantage of this alternative design is that the electrode struts are significantly compliant to the motion/contraction of the heart tissue, which enhances effective delivery of the pacing charge due to reduced fibrotic tissue growth.

Another alternative for the struts 60 contemplates forming them out of a material having a thickness sufficient to cause the struts 60 to essentially expand from a tight, in-line configuration which is predominant during normal implantation, to define a larger spacing between the respective struts 60 following implant. Thus, the approximate diameter of the myocardial electrode 50 during implantation may be approximately 1 millimeter, however, following implantation and relaxing of the tension on the suture thread 52, the struts 60 may expand such that the myocardial electrode 50 can become approximately 2 to 4 millimeters in effective diameter.

The myocardial electrode 50 is preferably from 0.3 millimeters to 2 centimeters in length and preferably has a total surface area of between 1 square millimeter and 8 square millimeters. In addition, the myocardial electrode 50 may be spaced from the epicardial pad 30 a distance of between approximately 0.1 and 5 centimeters. Utilizing this configuration, for a pediatric implant wherein the thickness of the myocardial wall is approximately 2 to 5 millimeters, the myocardial electrode 50 may be spaced approximately 0.5 millimeters below the epicardial surface. For an adult, having a myocardial wall thickness of approximately 2 centimeters, the myocardial electrode 50 may be embedded at approximately 0.5 centimeters below the epicardial surface. It should be noted however, that the configuration can be modified to allow the myocardial electrode 50 to be spaced a greater or shorter distance from the epicardial pad 30, and the depth of the myocardial electrode 50 may be adjusted so that it is closer to the internal myocardial wall than to the epicardial wall of the myocardium, depending upon the surgeon performing the implant.

As an additional consideration, the myocardial electrode may be inserted and pulled into a position proximate to the internal myocardial wall of the heart, thereby having the conductor segment 40 extending all of the way through the myocardium. This may be advantageous, for example to provide the advantages of a transvenously implanted pacing lead system without requiring implantation and transvenous insertion of an electrode into the ventricle or atrium. This technique for placement of a pacing electrode would be most beneficial in patients having severely blocked or damaged veins or other anatomical restrictions.

Figure 3:
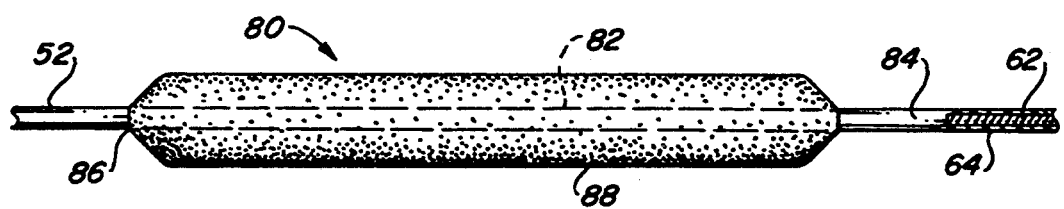
FIG. 3 depicts a first alternative embodiment of the myocardial electrode of FIG. 1.

FIG. 3 depicts an alternative embodiment for a myocardial electrode 80 contemplated by the present invention. The myocardial electrode 80 of FIG. 3 is formed from a single flexible electrode which may be formed, for example, from a platinum particle or titanium nitride coated single or multi-stranded cable or wire 82. The wire 82 may be simply an extension of the conductor 62 extending through the conductor segment 40 interconnected at the epicardial pad 30 to the conductor 28. In the design of FIG. 3, the wire 82 has a portion of the conductor 62 covered with insulation 84 to space the myocardial electrode 80 from the epicardial pad 30.

As in the embodiment of FIG. 2, the distal end 86 of the wire 80 of FIG. 3 is interconnected to a thread 52, which may be either bio-absorbable or non-bioabsorbable. The thread 52 is also interconnected to the suture needle 54, which allows the myocardial electrode 80 to be pulled into place in the myocardium. As further depicted in FIG. 3, the myocardial electrode 80 may be coated with a bioabsorbable and/or erodible anti-inflammatory material 88. The material 88 may be a gelatinous material which may include a therapeutic agent. Following implantation, the bioabsorbable or erodible material will gradually be absorbed by the surrounding myocardial tissue, and will prevent or reduce fibrotic growth and the normally occurring inflammatory response of the tissue to the myocardial electrode 80.

For either of the designs of FIGS. 2 and 3, the bioabsorbable coating materials 70 or 88 as well as the tablet 74 shown in FIG. 2, may be a material selected from the group including soluble starches such as amylodextrin and amylogen, proteins such as collagen, albumin and gelatin. These protein materials may be crosslinked with a crosslinking agent such as 1-ethyl-3-(3-dimethylaminopropyl), carbodiimide, hydrochloride. Additionally, the coating materials 70 or 88 may be ion exchange materials such as polyethylenimine, polysodium styrenesulfonates, and sulfonated polytetrafluoroethylene sold under the tradename NAFION by the DuPont Corporation. The foregoing materials are preferred because of the ability of the body to resorb them without adverse effect.

Polymeric systems selected from the group including polyethylene oxide or glycol, polypropylene oxide or glycol, polypropylene glycol, polysorbates, polyvinylalcohol, and copolymers of ethylene oxide/propylene oxide can also be used as the coating materials 70 or 88, and can deliver therapeutic agents by co-dissolution due to the inherent solubility of these materials.

The coating materials 70 or 88 is preferably a mixture of one of the above matrix materials blended with an anti-inflammatory agent selected from the group including fluoro-trihydroxy-methyl pregna diene/dione or fluoro-methylprednisolone, sodium phosphate, the sodium salt of methoxy-methyl-naphthalene-acetic-acid, sodium, or the sodium salt of isobutylphyl-propionic acid. The anti-inflammatory agents can constitute between about 1% to 95% by weight of the coating materials 70 or 88, preferably however, the anti-inflammatory agents constitute in the range of between 5% and 50% by weight of the coating materials 70 or 88.

FIG. 4 depicts a top view of the end of the myocardial lead 20 of FIG. 1. The top view clearly depicts the shape of the epicardial pad 30, which includes a pair of ears 34 and 36 which may include holes therethrough to allow the ears 34, 36 to be sutured to the epicardial tissue. In addition, a suture tie down groove 38 may be incorporated into the design of the epicardial pad 30 to allow better affixation of the epicardial pad 30 to the epicardial tissue. As further illustrated in FIG. 4, the myocardial electrode 50 is located distally a short distance from the epicardial pad 30, separated by an insulated conductor 40, and is interconnected to the thread 52 and suture needle 54.

FIG. 5 depicts the bottom view of the end of the myocardial lead 20 of FIG. 4. In the bottom view, the anode electrode 32 is clearly illustrated on the bottom surface of the epicardial pad 30. The anode electrode 32 is designed to be in intimate contact with the epicardial tissue once the epicardial pad 30 is secured in place. In this configuration, the lead body 22 includes at least two conductors 28 and 90 shown in FIG. 4, one extending to the anode electrode 32 as previously discussed and the other, e.g. conductor 90, extending to the myocardial electrode 50. The lead body 22 may include additional redundant conductors interconnected to the myocardial electrode 50 and the anode electrode 32 for use in the event of failure of a conductor. The two electrode design for the myocardial lead 20 allows bipolar pacing and/or sensing utilizing one of the electrodes, for example the myocardial electrode 50 as the cathode and the electrode 32 affixed to the epicardial pad 30 as the anode. It should be noted that the anode electrode 32, can be of any suitable shape or material.

Furthermore, it is contemplated that each of the struts 60 in the myocardial electrode 50 could be electrically interconnected to its own corresponding electrical conductor. Thus, the conductor segment 40 may include three or four separate insulated wires extending to the myocardial electrode 50. In this configuration, the individual struts 60 could be used as anodes, cathodes or electrical sensors, by proper programming of the pacemaker 26.

FIG. 6 depicts another alternative embodiment wherein a myocardial lead 100 includes two or more myocardial electrodes 104, 106 and associated connector segments 140 extending from a single epicardial pad 102. The designs of the respective myocardial electrodes 104, 106 of the embodiment of FIG. 7 may take the form of any of the detailed designs shown in FIGS. 2 and 3 and discussed above. It should be noted that while two myocardial electrodes 104, 106 are shown in FIG. 6, three or possibly four myocardial electrodes could be interconnected to a single epicardial pad 102. Further, all or some of a plurality of myocardial electrodes could be connected to separate conductors extending through the myocardial lead 100 which can act as different electrodes, i.e. either anodes or cathodes.

In view of the foregoing detailed description, it may be appreciated that the present invention contemplates an improved cardiac pacing system and method of pacing. The method of pacing a heart contemplates implanting a pulse generator, coupling a proximal end of a lead body to the pulse generator. The lead body having an electrical conductor, an insulation sheath covering the conductor, and an electrical connector affixed to its proximal end and a myocardial electrode assembly at its distal end. The myocardial electrode assembly is affixed to the heart to be paced, and includes an epicardial pad and an insulated conductor extending from the epicardial pad to a myocardial electrode. Pacing of the heart occurs upon coupling an electrical charge from the pulse generator through the lead body to the myocardial electrode to pace the heart.

The method further contemplates embedding the myocardial electrode of the myocardial electrode assembly into the myocardial tissue of the heart in either the ventricle or the atrium. The myocardial electrode includes at least one exposed electrically conductive element affixed at its proximal end to the insulated conductor. Alternatively, the embedded myocardial electrode may include a plurality of struts of electrically conductive metallic material, the struts being interconnected at their proximal ends to the insulated conductor. Accordingly, the method further contemplates forming the myocardial electrode according to a number of design factors and alternatives, as discussed in detail above. Further, the method of pacing may utilize a bipolar electrode configuration, wherein a second epicardial electrode is attached to the epicardial pad.

It should be evident from the foregoing description that the present invention provides many advantages over pacing leads and systems of the prior art. Although preferred embodiments are specifically illustrated and described herein, it will be appreciated that many modifications and variations of the present invention are possible in light of the above teaching to those skilled in the art. It is preferred, therefore, that the present invention be limited not by the specific disclosure herein, but only by the appended claims.

What is claimed is:

1. A myocardial lead for use with a desired cardiac pulse generator, comprising:
    an electrical conductor having a proximal end and a distal end;
    an insulation sheath covering said electrical conductor;
    an electrical connector coupled to said proximal end of said electrical conductor for electrically and mechanically interfacing with the pulse generator; and
    a myocardial electrode coupled to said distal end of said electrical conductor, said myocardial electrode comprising a plurality of struts, the struts being formed of electrically conductive material, said struts each having a distal end and a proximal end, the distal ends thereof being joined together, the proximal ends thereof being joined together and electrically interconnected to the electrical conductor.

2. The myocardial lead of claim 1, further comprising:
    coating means coating said myocardial electrode for reducing inflammation upon implant of the myocardial electrode, said coating means including a material selected from the group consisting of hydrogels, polymeric systems, soluble starches, proteins, glucocortico steroids and ion exchange materials.

3. The myocardial lead of claim 2, wherein said coating means further comprises a therapeutic agent.

4. The myocardial lead of claim 3, wherein said therapeutic agent is selected from the group consisting of fluoro-trihydroxy-methyl pregna diene/dione, fluoro-methylprednisolone, sodium phosphate, the sodium salt of methoxy-methyl-naphthalene-acetic-acid, sodium, and the sodium salt of isobutylphyl-propionic acid.

5. A myocardial lead for use with a desired cardiac pulse generator, comprising:
    a lead body having a proximal end and a distal end, the lead body comprising a first electrical conductor extending between the ends of the lead body, an insulation sheath covering first electrical said conductor, and an electrical connector affixed to the proximal end of said lead body for electrically interfacing with the pulse generator; and
    a myocardial electrode assembly affixed to said lead body, said myocardial electrode assembly including an epicardial pad and a myocardial electrodes, the myocardial electrode comprising
    a plurality of struts of electrically conductive metallic material, said struts each having a proximal end and a distal end, said struts being secured together at their distal ends, said struts being secured together at their proximal ends to said insulated conductor, said plurality of struts defining an open chamber therebetween.

6. The myocardial lead of claim 5, wherein said lead bond includes securing means comprising a bioabsorbable thread for securing together said distal ends of the struts.

7. The myocardial lead of claim 5, further comprising a suture thread and a suture needle affixed to the secured together distal ends of the struts for facilitating placement the myocardial electrode within the myocardium.

8. The myocardial lead of claim 5, wherein said myocardial electrode assembly further comprises:
    an epicardial electrode affixed to said epicardial pad; and
    means for electrically insulating the epicardial electrode form said myocardial electrode.

9. The myocardial lead of claim 8, further, comprising a second electrical conductor, wherein said epicardial electrode is electrically connected to the second conductor, said second conductor extending through said lead body to said electrical connector.

10. The myocardial lead of claim 5, wherein said myocardial electrode is spaced from said epicardial pad a distance comprising a range of about 0.1–5 cm.

11. The myocardial lead of claim 5, wherein said myocardial electrode has a length comprising a range of about 0.5 mm–2 cm and an electrically exposed surface area comprising a range of about 0.1 square millimeters–8 square millimeters.

12. The myocardial lead of claim 5, wherein said myocardial electrode is formed from material selected from the group consisting of titanium, platinum or platinum-iridium.

13. The myocardial lead of claim 12, wherein said cable of said myocardial electrode is a multifilar braided cable.

14. The myocardial lead of claim 5, wherein said mocardial electrode comprises a plurality of struts, each of said struts formed from material selected from the group consisting of titanium, platinum or platinum-iridium.

15. The myocardial lead of claim 14, further including
    a tablet of biocompatible material located within said open chamber defined by said plurality of struts.

16. The myocardial lead of claim 15, further comprising:
    a mesh of electrically conductive wire inserted in said open chamber defined by said plurality of struts, said mesh being electrically connected to said struts.

17. The myocardial lead of claim 14, wherein each of said struts has a particulate coating, said particulates selected from the group consisting of platinum black, titanium-nitride, and iridium oxide.

18. The myocardial lead of claim 5, wherein said plurality of of struts are movable relative to each other under the action of growing myocardial tissue.

19. A bipolar lead for use with a cardiac pacemaker comprising:

a lead body having a proximal end and a distal end, the lead body having first and second electrical conductors, an insulation sheath covering said at least two electrical conductors, and an electrical connector affixed to the proximal end of said lead body for electrically interfacing with the pacemaker; and an assembly affixed to the distal end of said lead body, said assembly including a myocardial electrode;

an epicardial pad having a first electrode affixed to an epicardial tissue facing surface; and an insulated conductor extending from said epicardial pad to the myocardial electrode, said myocardial electrode electrically connected to the first conductor and said epicardial pad electrode connected to the second electrical conductor comprising a plurality of struts of electrically conductive metallic material, said struts each having a proximal end and a distal end, said struts being secured together at their distal ends, said struts being secured together at their proximal ends to said insulated conductor, said plurality of struts further defining an open chamber therebetween.

20. The bipolar lead of claim 19, wherein said myocardial electrode and said epicardial pad electrode are separated by a distance comprising a range of about 0.1–5 cm.

21. The bipolar lead according to claim 19, further comprising means for embedding said myocardial electrode into the myocardium.

22. An implantable myocardial lead for use with a cardiac pacemaker comprising:

an electrical conductor having a proximal end and a distal end;

an insulation sheath covering said conductor;

an electrical connector affixed to said proximal end of said conductor;

a myocardial electrode assembly affixed to said distal end of said conductor, said electrode assembly having a myocardial electrode, an epicardial pad and an insulated conductor extending from said epicardial pad to the myocardial electrode comprising a plurality of struts of electrically conductive metallic material, said struts each having a proximal end and a distal end, said struts being secured together at their distal ends, said struts being secured together at their proximal ends to said insulated conductor, said plurality of struts defining an open chamber therebetween; and a coating material coating said myocardial electrode to prevent inflammation of the myocardial tissue while maintaining electrical conductivity between said myocardial electrode and the myocardial tissue, said coating material including a matrix material and a therapeutic agent blended into composition, wherein said matrix material of said coating material is a biocompatible material selected from the group consisting of poly-vinylpyrrolidone, poly-acrylamide, polyhydroxyethylmethacrylate, polyethylene oxide, polyethylene glycol, polypropylene glycol, polypropylene glycol, polysorbates, poly-vinylalcohol, copolymers of ethylene oxide/-propylene oxide, amylodextrin, amylogen, collagen, gelatin, polyethylenimine, poly-sodium styrenesulfonates, and sulfonated polytetrafluoroethylene, and said therapeutic agent of said coating material is selected from the group consisting of fluoro-trihydroxy-methyl pregna diene/dione, fluoro-methylprednisolone, sodium phosphate, the sodium salt of methoxy-methyl-naphthalene-acetic-acid, sodium, and the sodium salt of isobutylphyl-propionic acid and dexamethasone sodium phosphate.

23. A cardiac stimulation lead for use with an implantable pulse generator comprising:

a lead body having a proximal end and a distal end and a plurality of insulated electrical conductors, an electrical connector affixed to the proximal end of said lead body for electrically interfacing each one of the plurality of electrical conductors to said pulse generator; and a myocardial electrode assembly affixed to the distal end of said lead body, said myocardial electrode assembly having a myocardial electrodes, the myocardial electrode having a plurality of struts formed of electrically conductive material, each strut being electrically coupled to a respective one of the insulated conductors, whereby each of said struts can be selectively used as a cathode, an anode, and an electrode.

24. The myocardial lead of claim 23, wherein said myocardial electrode assembly includes an epicardial pad having an epicardial electrode adapted for contact with epicardial tissue, said epicardial electrode being electrically coupled to a respective one of the plurality of electrical conductors.

25. A mocardial stimulation lead for use with a pulse generator, comprising:

a lead body having a distal end and a proximal end, and a first insulted electrical conductor coupled therebetween;

a connector coupled to the lead body proximal end for electrically interfacing with the pulse generator; and a myocardial electrode comprising a plurality of compliant electrically conductive struts electrically coupled to the lead body distal end for transferring electrical signals between the pulse generator and myocardial tissue, the struts each having a distal end and a proximal end, the distal ends of the struts being joined together and the proximal ends of the struts being joined together.

26. The myocardial stimulation lead of claim 25, further comprising:

an epicardial pad secured to the lead body, the epicardial pad including means for securing the epicardial pad to epicardial tissue to thereby anchor the lead body to such epicardial tissue.-

27. The myocardial stimulation lead of claim 26, wherein the epicardial pad includes an epicardial electrode adapted for contact with epicardial tissue and wherein the lead body includes a second insulated electrical conductor electrically coupled between the epicardial electrode and the connector for transferring electrical signals between the epicardial electrode and the pulse generator.-

28. A myocardial stimulation lead for use with a pulse generator, comprising:

a lead body having a distal end and a proximal end and at least one insulated electrical conductor coupled therebetween;

a connector coupled to the lead body proximal end for electrically interfacing with the pulse generator; and a plurality of myocardial electrodes electrically coupled to the lead body distal end for transferring electrical signals between the pulse generator and myocardial tissue, each one of the plurality of myocardial electrodes comprising a plurality of electrically conductive struts, each strut having a distal end and a proximal end, the distal ends of the struts forming one myocardial electrode of the plurality of myocardial electrodes being joined together, the proximal ends of the struts forming such one myocardial electrode being joined together.

29. The myocardial stimulation lead of claim 28, wherein the at least one insulated conductor comprises a plurality of insulated conductors and wherein each one of the plurality of myocardial electrodes is electrically coupled to a respective one of the plurality of insulated conductors.

30. A myocardial stimulation lead for use with a pulse generator, comprising:
a lead body having a distal end and a proximal end, and an insulated electrical conductor coupled therebetween;
a connector coupled to the lead body proximal end for electrically interfacing with the pulse generator; and
a myocardial electrode comprising a plurality of compliant electrically conductive struts electrically coupled to the lead body distal end for transferring electrical signals between the pulse generator and myocardial tissue, the struts each having a distal end and a proximal end, the proximal ends being joined together and mechanically and electrically coupled to the insulated conductor; and
a bioabsorbable thread securing together the distal ends of the struts whereby upon absorption of the bioabsorbable thread, the distal ends will tend to space themselves apart one from one another under the action of myocardial tissue.

31. A myocardial stimulation lead for use with a pulse generator, comprising:
a lead body having a distal end and a proximal end, and an insulated electrical conductor coupled therebetween;
a connector coupled to the lead body proximal end for electrically interfacing with the pulse generator; and
a myocardial electrode comprising a plurality of compliant electrically conductive struts electrically coupled to the lead body distal end for transferring electrical signals between the pulse generator and myocardial tissue, the struts each having a distal end and a proximal end, the distal ends being joined together and the proximal ends being joined together; and
means coupled to the distal ends of the struts for applying a force to the myocardial electrode for urging the myocardial electrode into myocardial tissue such that urging the myocardial electrode into myocardial tissue causes the struts to compress to a tight essentially in-line configuration and whereupon release of the urging force causes the struts to expand in a direction away from each other.

32. The myocardial stimulation lead of claim 31, further comprising an epicardial pad secured to the lead body, the epicardial pad including means for securing the epicardial tissue.

33. The myocardial stimulation lead of claim 32, wherein the epicardial pad includes an epicardial electrode adapted for contact with epicardial tissue and wherein the lead body includes a second insulated electrical conductor electrically coupled between the epicardial electrode and the connector for transferring electrical signals between the epicardial electrode and the pulse generator.

* * * * *